United States Patent
Avni et al.

(10) Patent No.: US 7,664,174 B2
(45) Date of Patent: Feb. 16, 2010

(54) DIAGNOSTIC DEVICE, SYSTEM AND METHOD FOR REDUCED DATA TRANSMISSION

(75) Inventors: Dov Avni, Haifa (IL); Gavriel Meron, Petach Tikva (IL); Eli Horn, Kiryat Motzkin (IL); Ofra Zinaty, Haifa (IL); Arkady Glukhovsky, Santa Clarita, CA (US)

(73) Assignee: Given Imaging, Ltd., Yoqneam (IL)

( * ) Notice: Subject to any disclaimer, the term of this patent is extended or adjusted under 35 U.S.C. 154(b) by 0 days.

(21) Appl. No.: 10/551,436

(22) PCT Filed: Mar. 29, 2004

(86) PCT No.: PCT/IL2004/000287

§ 371 (c)(1),
(2), (4) Date: Jul. 17, 2006

(87) PCT Pub. No.: WO2004/088448

PCT Pub. Date: Oct. 14, 2004

(65) Prior Publication Data

US 2006/0262186 A1    Nov. 23, 2006

(30) Foreign Application Priority Data

Mar. 31, 2003    (IL) .................................... 155175

(51) Int. Cl.
- H04N 7/12    (2006.01)
- H04N 11/02   (2006.01)
- H04N 11/04   (2006.01)
- H04B 1/66    (2006.01)

(52) U.S. Cl. ................................. 375/240.01
(58) Field of Classification Search ............ 375/240.01
See application file for complete search history.

(56) References Cited

U.S. PATENT DOCUMENTS

| | | | |
|---|---|---|---|
| 3,971,362 A | | 7/1976 | Pope et al. |
| 4,278,077 A | | 7/1981 | Mizumoto |
| 4,689,621 A | | 8/1987 | Kleinberg |
| 4,689,689 A | | 8/1987 | Saito et al. |
| 4,834,070 A | * | 5/1989 | Saitou .................... 600/108 |
| 4,844,076 A | | 7/1989 | Lesho et al. |

(Continued)

FOREIGN PATENT DOCUMENTS

DE    3440177    5/1986

(Continued)

OTHER PUBLICATIONS

U.S. Appl. No. 60/307,605, filed Jul. 26, 2001, Glukhovsky et al.

(Continued)

*Primary Examiner*—Nhon T Diep
(74) *Attorney, Agent, or Firm*—Pearl Cohen Zedek Latzer, LLP

(57) ABSTRACT

A device, system and method may enable the obtaining of in vivo images from within body lumens or cavities, such as images the gastrointestinal (GI) tract, where the data such as image data is typically transmitted or otherwise sent to a receiving system in compressed or diluted form. The image may be reconstructed and for example displayed to a user.

15 Claims, 8 Drawing Sheets

U.S. PATENT DOCUMENTS

| | | | |
|---|---|---|---|
| 5,032,913 A * | 7/1991 | Hattori et al. | 348/70 |
| 5,209,220 A | 5/1993 | Hiyama et al. | |
| 5,279,607 A | 1/1994 | Schentag et al. | |
| 5,467,413 A | 11/1995 | Barrett | |
| 5,523,786 A * | 6/1996 | Parulski | 348/269 |
| 5,594,497 A | 1/1997 | Ahern et al. | |
| 5,604,531 A | 2/1997 | Iddan et al. | |
| 5,751,340 A | 5/1998 | Strobl et al. | |
| 5,798,846 A | 8/1998 | Tretter | |
| 5,819,736 A | 10/1998 | Avny et al. | |
| 5,956,467 A | 9/1999 | Rabbani et al. | |
| 5,987,179 A | 11/1999 | Riek et al. | |
| 5,993,378 A | 11/1999 | Lemelson | |
| 5,999,662 A | 12/1999 | Burt et al. | |
| 6,014,727 A | 1/2000 | Creemer | |
| 6,124,888 A * | 9/2000 | Terada et al. | 348/302 |
| 6,125,201 A | 9/2000 | Zador | |
| 6,167,084 A | 12/2000 | Wang et al. | |
| 6,184,922 B1 * | 2/2001 | Saito et al. | 348/65 |
| 6,229,578 B1 | 5/2001 | Acharya et al. | |
| 6,240,312 B1 | 5/2001 | Alfano et al. | |
| 6,304,284 B1 | 10/2001 | Dunton et al. | |
| 6,314,211 B1 * | 11/2001 | Kim et al. | 382/285 |
| 6,356,276 B1 | 3/2002 | Acharya | |
| 6,414,996 B1 | 7/2002 | Owen et al. | |
| 6,452,633 B1 | 9/2002 | Merrill et al. | |
| 6,492,982 B1 * | 12/2002 | Matsuzaki et al. | 345/204 |
| 6,498,948 B1 | 12/2002 | Ozawa et al. | |
| 6,501,862 B1 * | 12/2002 | Fukuhara et al. | 382/249 |
| 6,600,517 B1 * | 7/2003 | He et al. | 348/625 |
| 6,661,463 B1 * | 12/2003 | Geshwind | 348/384.1 |
| 6,937,291 B1 | 8/2005 | Gryskiewicz | |
| 6,939,290 B2 | 9/2005 | Iddan | |
| 6,972,791 B1 * | 12/2005 | Yomeyama | 348/230.1 |
| 7,044,908 B1 | 5/2006 | Montalbo et al. | |
| 7,057,664 B2 * | 6/2006 | Law et al. | 348/448 |
| 7,116,352 B2 | 10/2006 | Yaron | |
| 7,209,170 B2 * | 4/2007 | Nishino et al. | 348/302 |
| 7,236,191 B2 | 6/2007 | Kalevo et al. | |
| 7,319,781 B2 | 1/2008 | Chen et al. | |
| 7,495,993 B2 | 2/2009 | Wang | |
| 2001/0035902 A1 | 11/2001 | Iddan et al. | |
| 2002/0103417 A1 | 8/2002 | Gazdzinski | |
| 2002/0177779 A1 | 11/2002 | Adler et al. | |
| 2002/0198439 A1 | 12/2002 | Mizuno et al. | |
| 2003/0020810 A1 | 1/2003 | Takizawa et al. | |
| 2003/0023150 A1 | 1/2003 | Yokoi et al. | |
| 2003/0043263 A1 | 3/2003 | Glukhovsky et al. | |
| 2003/0060734 A1 | 3/2003 | Yokoi et al. | |
| 2003/0085994 A1 | 5/2003 | Fujita et al. | |
| 2003/0156188 A1 * | 8/2003 | Abrams, Jr. | 348/51 |
| 2003/0158503 A1 | 8/2003 | Matsumoto | |
| 2003/0181788 A1 | 9/2003 | Yokoi et al. | |
| 2003/0213495 A1 | 11/2003 | Fujita et al. | |
| 2003/0216670 A1 | 11/2003 | Beggs | |
| 2003/0229268 A1 | 12/2003 | Uchiyama et al. | |
| 2004/0215059 A1 | 10/2004 | Homan et al. | |
| 2004/0225190 A1 | 11/2004 | Kimoto et al. | |
| 2004/0225223 A1 * | 11/2004 | Honda et al. | 600/476 |
| 2004/0242962 A1 | 12/2004 | Uchiyama et al. | |
| 2005/0159643 A1 | 7/2005 | Zinaty et al. | |

FOREIGN PATENT DOCUMENTS

| | | |
|---|---|---|
| JP | 4109927 | 4/1992 |
| JP | 5015515 | 1/1993 |
| JP | 6-038201 | 2/1994 |
| JP | 11-211997 | 8/1999 |
| JP | 2000/358242 | 12/2000 |
| JP | 2003/070728 | 3/2003 |
| WO | WO 01/50941 | 7/2001 |
| WO | WO 01/65995 | 9/2001 |
| WO | WO 03/010967 | 2/2003 |
| WO | WO 2004/088448 | 10/2004 |

OTHER PUBLICATIONS

The Radio Pill, Rowlands, et al., British Communications and Electronics, Aug. 1960, pp. 598-601.

Wellesley company sends body montiors into space—Crum, Apr. 1998.

Wireless transmission of a color television moving image from the stomach using a miniature CCD camera, light source and microwave transmitter. Swain CP, Gong F, Mills TN. Gastrointest Endosc 1997;45:AB40.

BBC News Online—Pill camera to 'broadcast from the gut', Feb. 21, 2000, www.news.bbc.co.uk.

Biomedical Telemetry, R. Stewart McKay, published by John Wiley and Sons, 1970.

International Search Report for PCT/IL2004/00287 dated Mar. 16, 2005.

International Search Report for PCT/IL02/00621 dated Dec. 6, 2002.

Office Action for U.S. Appl. No. 11/087,606 mailed Mar. 31, 2009.

Office Action for U.S. Appl. No. 10/991,098 mailed on Jul. 6, 2009.

Final Office Action for U.S. Appl. No. 11/087,606 mailed on Aug. 28, 2009.

Japanese Office Action of Application No. 2003-516219 mailed on Aug. 12, 2008.

Korean Office Action of Application No. 10-2004-7001173 mailed on Nov. 26, 2008.

* cited by examiner

DIAGNOSTIC DEVICE, SYSTEM AND METHOD FOR REDUCED DATA TRANSMISSION

CROSS-REFERENCE TO RELATED APPLICATIONS

This application is a National Phase Application of PCT International Application No. PCT/IL2004/000287, International Filing Date 29 Mar. 2004, claiming priority of Israeli Patent Application IL 155175, filed 31 Mar. 2003, which are hereby incorporated by reference in their entirety.

FIELD OF THE INVENTION

The present invention relates to an in vivo device, system and method such as for imaging the digestive tract; more specifically, to an in vivo device, system and method where information transmitted or sent, is compressed.

BACKGROUND OF THE INVENTION

Devices and methods for performing in-vivo imaging of passages or cavities within a body, and for gathering information other than or in addition to image information (e.g., temperature information, pressure information), are known in the art. Such devices may include, inter alia various endoscopic imaging systems and devices for performing imaging in various internal body cavities.

An in-vivo imaging device may include, for example, an imaging system for obtaining images from inside a body cavity or lumen, such as the GI tract. The imaging system may include, for example, an illumination unit, such as a set of light emitting diodes (LEDs), or other suitable light sources. The device may include an imaging sensor and an optical system, which focuses the images onto the imaging sensor. A transmitter and antenna may be included for transmitting the images signals. A receiver/recorder, for example worn by the patient, may record and store image and other data. The recorded data may then be downloaded from the receiver/recorder to a computer or workstation for display and analysis. Such imaging and other devices may transmit data such as image data or other data during a certain period of time. It may be desirable to limit the amount of time spent transmitting image data, and also the bandwidth required for such a transmission. The time spent transmitting limits the amount of image or other data that may be transmitted. Other in-vivo diagnostic units need not transmit by radio waves, for example, image or other data collected may be sent via wire.

Therefore, there is a need for an in-vivo diagnostic device, such as an imaging device, which more efficiently transmits data.

SUMMARY OF THE INVENTION

An embodiment of the device, system and method of the present invention enables the obtaining of in vivo images from within body lumens or cavities, such as images of the gastrointestinal (GI) tract, where the data such as image data is typically transmitted or otherwise sent to a receiving system. According to one embodiment of the invention, the data transmitted, including, for example, image information, is compressed. The data may be reconstructed using suitable methods and, for example, displayed to a user.

DETAILED DESCRIPTION OF EMBODIMENTS OF THE INVENTION

Figure 1A:
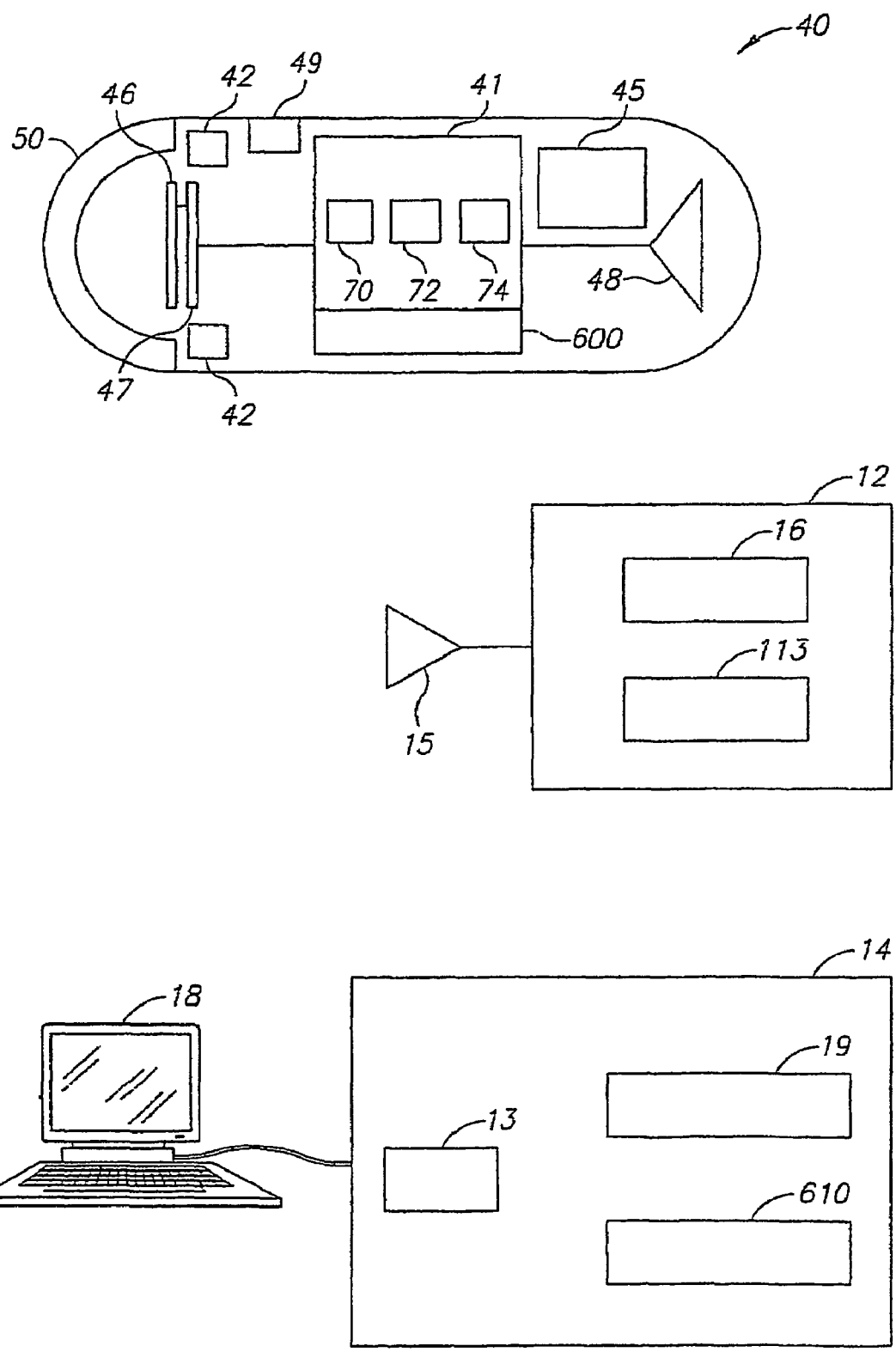
FIG. 1A shows a schematic diagram of an in vivo imaging system according to one embodiment of the present invention.
Figure 1B:
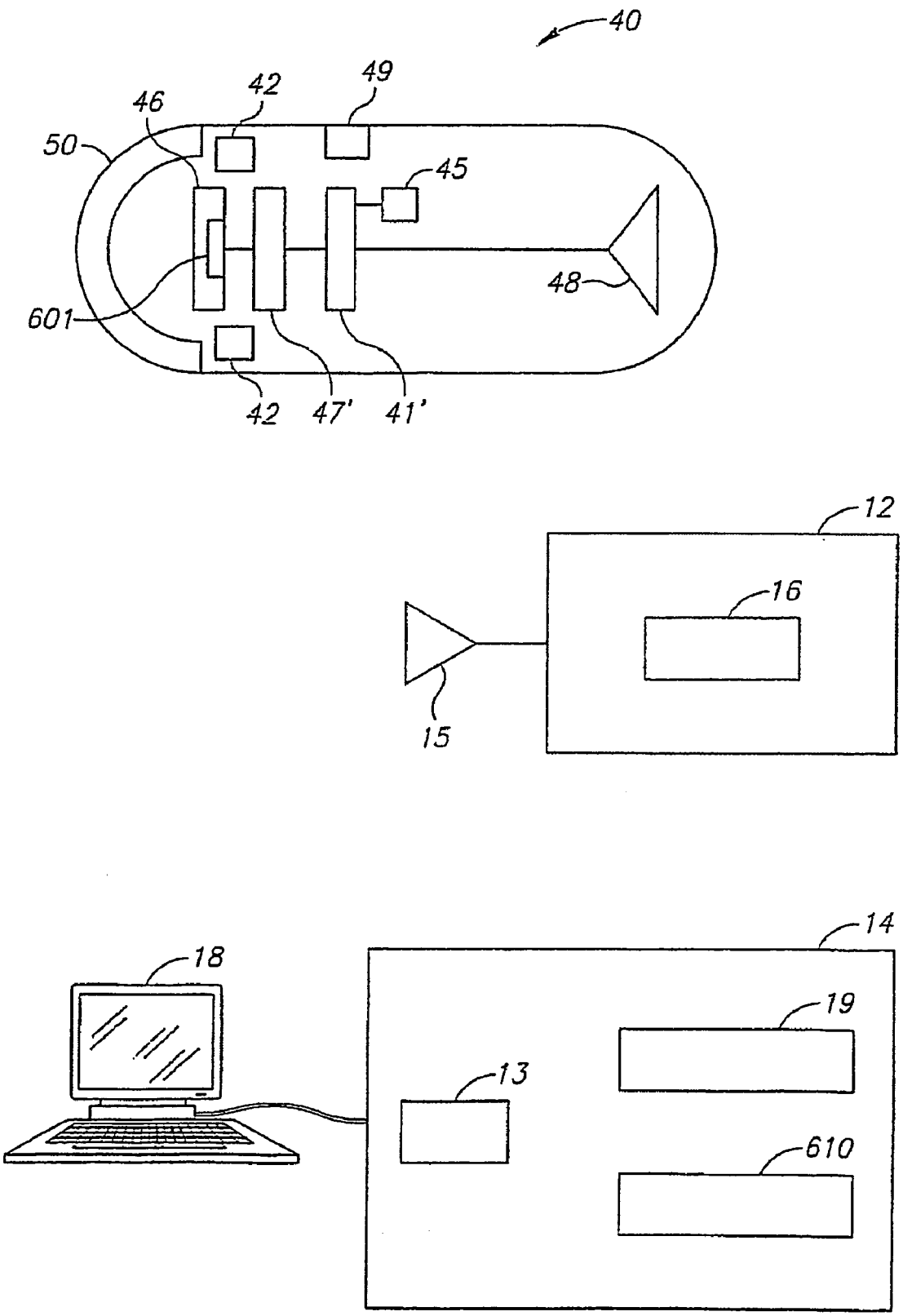
FIG. 1B shows a schematic diagram of an in vivo imaging system according an embodiment of the present invention.
Figure 1C:
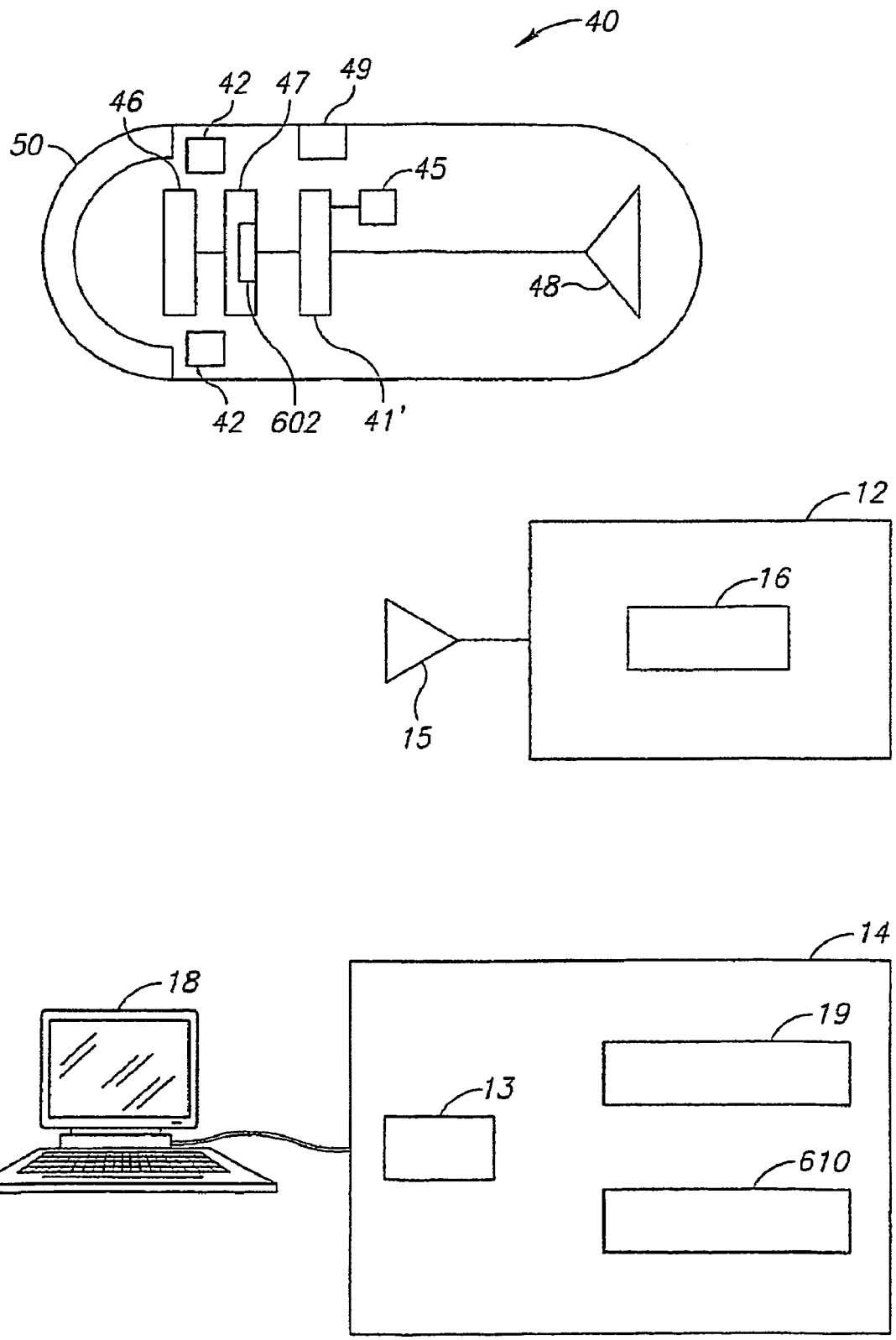
FIG. 1C shows a schematic diagram of an in vivo imaging system according an embodiment of the present intention.
Figure 1D:
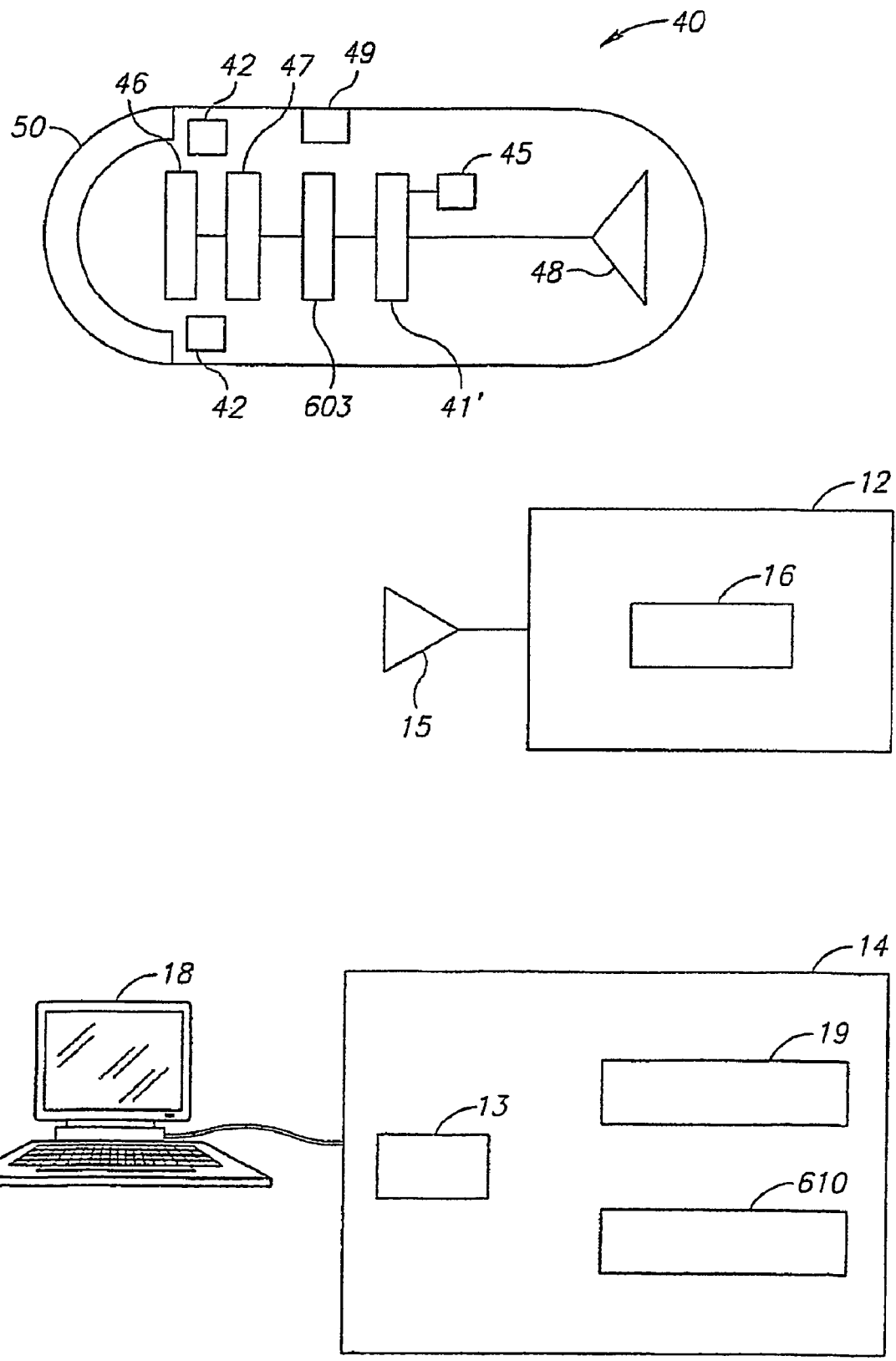
FIG. 1D shows a schematic diagram of an in vivo imaging system according to an embodiment of the present invention.

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Embodiments of the system and method of the present invention may be preferably used in conjunction with an imaging system or device such as described in U.S. Pat. No. 5,604,531 to Iddan et al. and/or in application number WO 01/65995 entitled "A Device And System For In Vivo Imaging", published on 13 Sep., 2001, both of which are hereby incorporated by reference. However, the device, system and method according to the present invention may be used with any device providing imaging or, other data from a body lumen or cavity. In alternate embodiments, the system and method of the present invention may be used with devices capturing information other than image information within the human body; for example, temperature, pressure or pH information, information on the location of the transmitting device, or other information.

Reference is made to FIGS. 1A-1D, which show schematic diagrams of in vivo imaging system according to embodiments of the present invention. In an exemplary embodiment shown in FIG. 1A, a device 40 may be an ingestible capsule capturing images, but may be another sort of device and may collect information other than image information. Typically, device 40 may include at least one sensor such as an imager 46, for capturing images, a processing chip or circuit 47 that processes the signals generated by the imager 46, and one or more illumination sources 42, for example one or more "white LEDs" or any other suitable light source, for illuminating the body lumen. An optical system 50, including, for example, one ox more optical elements (not shown), such as one or more lenses or composite lens assemblies (not shown), one or more suitable optical filters (not shown), or any other suitable optical elements (not shown), may aid in focusing reflected light onto the imager 46 and performing other light processing. Processing chip 47 need not be a separate component; for example, processing or a processing chip may be integral to the imager 46. A non-image sensor 49, for example, such as a temperature sensor, a pH sensor, or a pressure sensor may be included. In an alternate embodiment of the present invention sensor 46 may be a non-image sensor such as a temperature sensor, a pH sensor, or a pressure sensor.

Device 40 typically includes a transmitter 41, for transmitting image and possibly other information (e.g., control information, non-image data, etc.) to a receiving device, and a compression module 600, for compressing data. The transmitter 41 may typically be an ultra low power radio frequency (RF) transmitter with high bandwidth input, possibly provided in chip scale packaging. The transmitter may transmit via an antenna 48. The transmitter 41 may act as a controller may also include circuitry and functional for controlling the device 40. Typically, the device may include a power source 45, such as one or more batteries. For example, the power source 45 may include silver oxide batteries, lithium batteries, or other electrochemical cells having a high energy density, or the like. Other suitable power sources may be used.

Other components and sets of components may be used. For example, the power source may be an external power source transmitting power to the capsule, for example as described in a patent application with International Publication Number WO 02/080753 A2, and a controller separate from the transmitter 41 may be used.

In one embodiment, the imager 46 may be a complementary metal oxide semiconductor (CMOS) imaging camera. The CMOS imager may typically be an ultra low power imager and may be provided in chip scale packaging (CSP). One suitable CMOS camera may be, for example, a "camera on a chip" CMOS imager specified by Given Imaging Ltd. of Israel and designed by Photobit Corp. of California, USA, with integrated active pixel and post processing circuitry. Other types of CMOS imagers may be used. In another embodiment, another imager may be used, such as a CCD imager, or another imager.

Typically, the device 40 is swallowed by a patient and traverses a patient's GI tract, however, other body lumens or cavities, such as blood vessels, the female reproductive tract, etc., may be imaged or examined. The device 40 transmits image and possibly other data to components located outside the patient's body, which may receive and process the data. Preferably, located outside the patient's body in one or more locations, may be a receiver 12, preferably including or attached to an antenna or antenna array 15, for receiving image and possibly other data from device 40, and a controller or processor 113, a receiver storage unit 16, for storing image and other data, a data processor 14, a data processor storage unit 19, a data decompression module 610 for decompressing data, and an image monitor 18, for displaying, inter alia, the images or reconstructed versions of the images transmitted by the device 40 and recorded by the receiver 12. Typically, the receiver 12 and receiver storage unit 16 may be small and portable, and may be worn on the patient's body during recording of the images. Preferably, data processor 14, data processor storage unit 19 and monitor 18 may be part of a personal computer or workstation, which includes, for example, standard components such as a processor 13, a memory (e.g., storage 19, or other memory), a disk drive, and input-output devices, although alternate configurations are possible. In alternate embodiments, the data reception and storage components may be of another suitable configuration. Further, image and other data may be received in other manners, by other sets of components. Typically, in operation, image data may be transferred to the data processor 14, which, in conjunction with processor 13 and software, may store, possibly process, and display the image data on monitor 18. Other systems and methods of storing and/or displaying collected image data may be used. Any of data processor 14, processor 13, receiver 12, controller 113, or another component or set of components, may act as or include a suitable controller or processor for, inter alia, controlling the receipt and transfer of data, reconstructing data decompressing data, etc.

Typically, the device 40 transmits image information in discrete portions. Each portion typically corresponds to an image or frame. Other transmission methods are possible. For example, the device 40 may capture an image once every half second, and, after capturing such an image, may transmit the image to the receiving antenna. Other capture rates may be possible. Typically, the image data recorded and transmitted may be a digital color image data, although in alternate embodiments other image formats (e.g., black and white image data) may be used. In one embodiment, each frame of image data includes 256 rows of 256 pixels each, each pixel including data for color and brightness, according to known methods. For example, in each pixel, color may be represented by a mosaic of four sub-pixels, each sub-pixel corresponding to primaries such as red, green, or blue (where one primary is represented twice). In other embodiments, each pixel may capture only one color. The brightness of the overall pixel may be recorded by, for example, a one byte (i.e., 0-255) brightness value. Other data formats may be used.

In some embodiments of the device, system and method of the present invention, diagnostic data need not be transmitted, but may be sent via another method, such as via wire. For example, in an endoscope device, an imaging device at one end may send the data via wire to a receiving device.

It may be desirable to limit the amount of time spent transmitting image data, and/or the bandwidth required for such a transmission. Embodiments of the system and method of the present invention may compress image and possibly other data before transmission. Since compressed data may take less time to transmit, more data may be transmitted, and more frames of image data may be translated per time unit, without increasing, foe example, the bandwidth of the transfer. Alternatively, the same amount of data may be transmitted using less bandwidth. Another aspect of the data transmission relates to the transmission systems with limited energy source. In this case smaller amount of bits needed to be transmitted may enable more energy per bit in the transmission. Data other than or in addition to image data may be transmitted and compressed. For example, control information may be compressed. Furthermore, in devices transmitting telemetric information other than image information, such as pressure or pH information, such information may be compressed. In further embodiments, image data need not be transmitted in discrete portions corresponding to images.

Thus, for example, if the bandwidth of a transmission mechanism permits an uncompressed frame relay rate of, for example, two frames per second at a specified bit rate, the same transmission mechanism may be able to support the transmission of a greater number of frames per second using the same bit rate if the transmitted data is compressed or diluted prior to compression, and then reconstructed after transmission. Thus, according to one embodiment, for areas of the gastro-intestinal tract where a greater number of frames per second may be desired (for example, the esophagus, which may be traversed quickly by a capsule), the imaging device may operate in a "fast mode" which transmits compressed or diluted data and may therefore be capable of transmitting a greater number of frames per second than uncompressed data. In one embodiment, data may be added by for example interpolation and/or other methods to produce completed images or images that may be presented as completed images.

In an exemplary embodiment of the present invention, device 40 includes a data compression module 600 for compressing data transmitted from the device 40 and for providing the data to the transmitter 41, possibly via intermediate circuitry. Data compression module 600 may be implemented as part of a microprocessor or ASIC or other micro-computing device, as part of the imager 46 or processing chip 47, or in another suitable manner. In alternate embodiments the functions of the data compression module 600 may be taken up by other structures and may be disposed in different parts of the device 40. For example, the transmitter 41 may include data compression capability, or data compression module 600 may be a stand-alone unit, or may be implemented in software. In one embodiment, transmitter 41 may include, for example, a modulator 70 for receiving the video signal from the imager 46, a radio frequency (RF) amplifier 72, and an impedance matcher 74. The modulator may convert the input image signal having a cutoff frequency of, for example, $f_c$ of less than 5 MHz to an RF signal having a carrier frequency $f_r$, typically in the range of 1 GHz (other ranges may be used). While in one embodiment the signal is an analog video signal, the modulating signal may be another signal, for example digital rather than analog. The carrier frequency may be in other bands, e.g. a 400 MHz band. The modulated RF signal may have a bandwidth of $f_r$. The impedance matcher may match the impedance of the circuit to that of the antenna. Other suitable transmitters or arrangements of transmitter components may be used, utilizing different signal formats and frequency ranges. For example, alternate embodiments may not include a matched antenna or may include a transmitter without a matching circuit. In one embodiment of such an imaging device 40, transmission may occur at a frequency of 434 MHz, using Phase Shift Keying (PSK). In alternate embodiments, other transmission frequencies and methods (such as AM or FM) may be used.

The receiver 12 may preferably detect a signal having the carrier frequency $f_r$ and the bandwidth $f_c$ described herein. The receiver 12 may be similar to those found in televisions or for example it may be one similar to those described on pages 244-245 of the book Biomedical Telemetry by R. Stewart McKay and published by John Wiley and Sons, 1970. The receiver may be digital or analog. In alternate embodiments, other receivers, responding to other type of signals, may be used.

The receiver 12 preferably includes a data decompression module 610 for decompressing data received from the device 40. In exemplary embodiment data decompression module 610 may be a microprocessor or other micro-computing device and may be part of the receiver 12. In alternate embodiments the functions of the data decompression (decoding) module 610 may be taken up by other structures and may be disposed in different parts or more than one part of the system; for example, data decompression module 610 may be implemented in software and/or be part of data processor 14. The receiver 12 may receive compressed data without decompressing the data and store the compressed data in the receiver storage unit 16. The data may be later decompressed by, for example data processor 14.

Preferably, the transmitter 41 may provide overall control of the device 40; in alternate embodiments control may be provided by other modules. Preferably, the data compression module 600 may interface with the transmitter 41 to receive and compress image data; other units may provide other data to data compression module 600. In addition, the data compression module 600 may provide the transmitter 41 with information such as, for example, start or stop time for the transfer of image data from the data compression module 600 to the transmitter 41, the length or size of each block of such image data, and the rate of frame data transfer. The interface between the data compression module 600 and the transmitter 41 may be handled, for example, by the data compression) module 600. Typically, the data compression module 600 may compress image information in discrete portions. Each portion may typically correspond to an image or frame. Other compression methods or sequences are possible, and other units of compression and transmission are possible. In one embodiment, to compress the image data, subsequent images may be compared, and to only differences between these images may be transmitted rather than each image. Assuming that in most cases the subsequent images may be similar, the difference between the images may contain much less information than the image itself.

In alternate embodiments, the data exchanged between the data compression module 600 and the transmitter 41 may be different, and in different forms. For example, size information need not be transferred. Furthermore, in embodiments having alternate arrangements of components, the interface and protocol between the various components may also differ. For example, in an embodiment where a data compression capability is included in the transmitter 41 and the imager 46 transfers uncompressed data to the transmitter 41, no start/stop or size information may be transferred. In another embodiment of the invention, a data compression module 601 may be implemented as part of an imager 46', such as in for example, device 40 shown in FIG. 1B. In one embodiment of the invention, imager 46' or another component within device 40 may produce a selection of input data to form a diluted image. In such a case, a transmitter 41' may be a transmitter without compression capability; however, using selections of data and compression may be performed together. In another embodiment of the invention, a compression module 602 may be part of a processing chip 47' such as in for example, device 40 shown in FIG. 1C. Processing chip 47 and 47' may be for example, a microprocessor, ASIC, or another suitable micro-computing device. In yet another embodiment of the invention, a compression module 603 may be included as a stand-alone unit such as in for example, device 40 shown in FIG. 1D.

The data compression module for example, module 600 (or 601, 602 or 603), and data decompression module 610, may use various data compression formats and systems. Compression formats used may include compression formats where some data may be lost during compression and compression formats where data may not be lost during compression. Typically, the data compression module 600 and decompression module 610 may include circuitry and/or software to perform such data compression. For example, if the data compression module 600 or decompression module 610 (or other compression or decompression systems) are implemented as a computer on a chip or ASIC, data compression module 600 or decompression module 610 may include a processor operating on firmware which includes suctions for a data compression algorithm. If data decompression module 610 is implemented as part of data processor 14 and/or processor 13, the decompression may be implemented as part of a software program. It will be evident to those of skill in the art that compression module need not be a physically separate component, but rather, that its functionality may be performed by another component, such as imager 46'.

The amount of imager data to be sent may be, for example, over 1.35 Megabits per second. Compression may reduce this amount. After compression, and before transmission, other operations such as randomization may occur (performed, for example, by the transmitter 41). For example, he occurrence of the digital signals ("0" and "1") may be randomized so that transmission may not be impeded by a recurring signal of one type.

Figure 2:
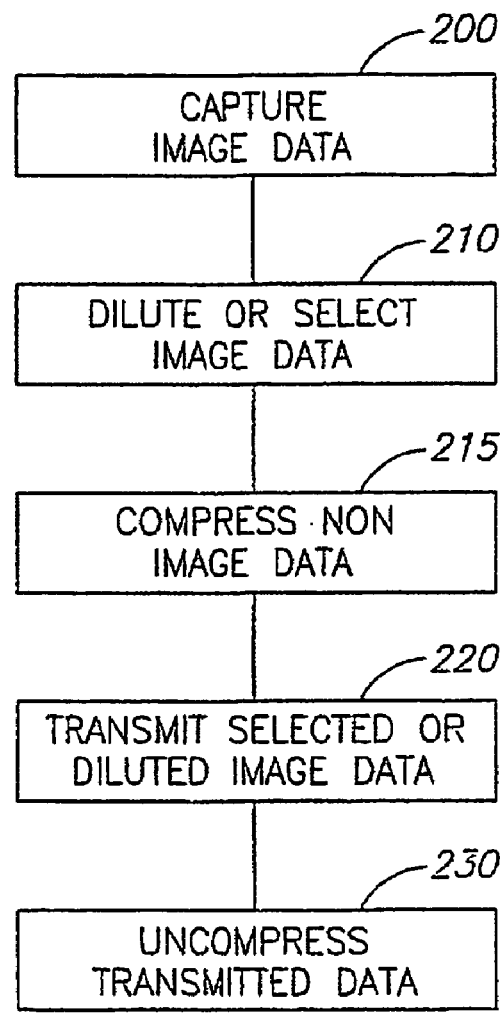
FIG. 2 depicts a series of steps of a method according to an embodiment of the present invention.

FIG. 2 depicts a series of steps of a method according to an embodiment of the present invention. Referring to FIG. 2, in block 200, an in-vivo device, such as a swallowable capsule, captures image data. Typically, an imager within the device may capture image data of a gastrointestinal tract, but other image data may be captured, for example, image data from other body lumens or cavities. Data other than or in addition to image data may be captured. The image data from the imager may be passed to other units for processing.

In block 210, the image data is compressed. Such compression or other processing may be performed by a processing unit such as, for example, transmitter 41. The image data is typically received from the imager or via another unit. Such compression may be typically in response to a process receiving input data corresponding to an image. In the embodiment shown in FIG. 2, compression may be accomplished by diluting the captured data, or by selecting only a pattern of pixels for transmission. Such creation of a selection of data, where the selection is typically less data than the original data, may be, for example, performed according to a dilution pattern. Alternately, only the differences between for example, pixels or regions of subsequent images may be transferred. The image data may be first loaded or transferred from the imager to a compression module, or, alternately or additionally, may be compressed at the imager. If applicable, data other than or in addition to image data may be compressed; in block 215, for example, sensor data other than image sensor data, control data, etc. In one embodiment of the invention, for example, data may be selected for transmission by the imager and then further compressed, for example, by JPEG or another algorithm before transmission. The selected data is typically less data than the original data.

In block 220, the data may be transmitted to a receiver. Typically, the data, such as for example image data, may be transmitted, for example, using radio waves (RF channel) to a receiver external to the body, but other methods may be used. In alternate embodiments, the image or other data may be sent by other methods, such as by wire.

In block 230, the data may be decompressed, enabling reconstruction of the image. Reconstruction may include further elements such as pre-processing, post-processing, etc. Reconstructed image data may be, for example, displayed or stored for later use. Alternately, the compressed image data may be stored for later image reconstruction.

Other suitable steps or series of steps may be used than those described in the above blocks.

The data compression methods described herein may be lossless or lossy. Loseless data compression may enable precise (with no distortion) decoding of the compressed data. The compression ratio of loseless methods may however be limited. Lossy compression methods may not enable precise decoding of the compressed information. However the compression ration of lossy methods may be much higher than of the lossless method. En many cases the data distortion of the lossy methods may be nonsignificant, and the compress ratio may be high. Without limitation of generality, the description of data compression schemes herein may be applicable both to lossless and to lossy methods.

In an embodiment of the present invention, compression may be accomplished by transmitting only portions of the captured image selected according to, for example, a dilution pattern. While this may result in some loss of quality in the resulting image, proper selection of pixels according to a suitable dilution pattern, together with proper reconstruction of the diluted image, may preserve the quality of the transmitted image and rehabilitate the image to lossless or near-lossless condition. The dilution pattern may for example be predetermined, may be selected or created by a component of the device based on operating conditions related, for example, to its position in the gastro-intestinal tract or other surrounding conditions such as pH, temperature, ambient lighting or color conditions, or may be created using other methods. Data may be selected for transmission by means other than a dilution pattern.

Embodiments of the invention are presented herein with different dilution patterns, although those of skill in the art will recognize that other dilution patterns may be used for compressed transmission in accordance with the present invention. In the below exemplary dilution patterns presented, there is assumed an imager with 256 rows and 256 columns of pixels, each pixel representing one of the colors red, blue or green. The embodiments also show an imager having twice as many green pixels as red or blue pixels. It will be recognized by those of skill in the art that the invention may be practiced with imagers of different configurations, sizes, and color patterns. For example, a black and white imager may be used.

Figure 3:
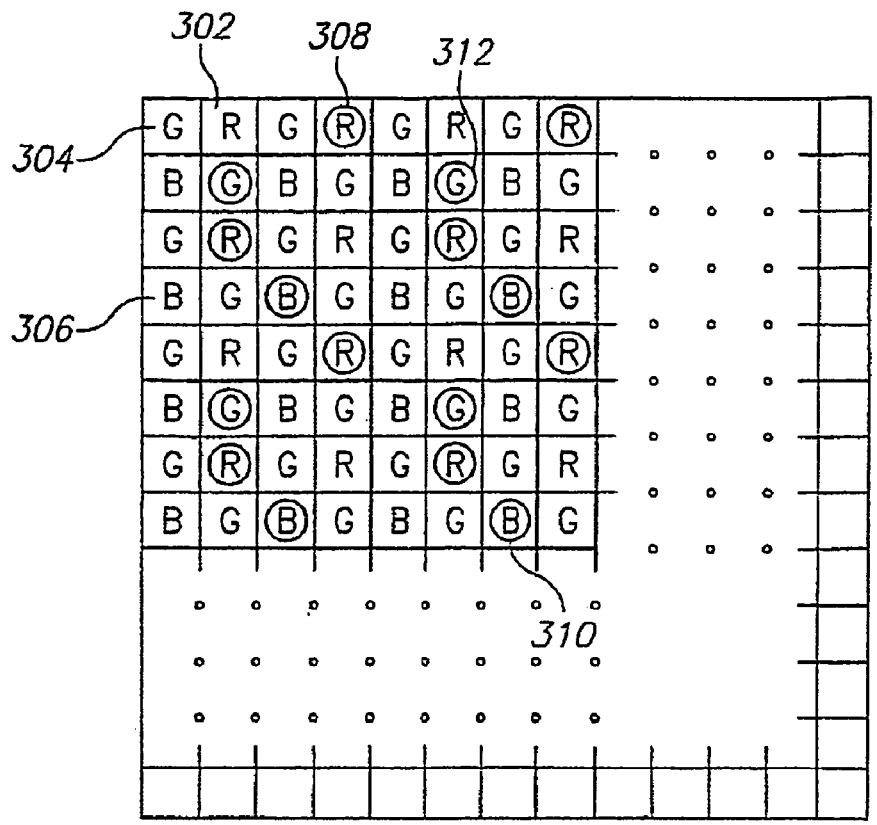
FIG. 3 depicts a schematic diagram of a first exemplary dilution pattern for selecting pixels according to an embodiment of the present invention.

FIG. 3 depicts one exemplary dilution pattern in accordance with embodiments of the invention that may be used in an imager having, for example, pixels representing red (R) 302, green (G) 304, and blue (B) 306 in the arrangement shown. In this first exemplary dilution pattern shown, the imaging device may transmit every, for example, fourth pixel in each row, where, typically, all pixels chosen in any row represent the same color. In the case of three colors, e.g., red, blue and green, one color selected for transmission may repeat every second row, while the selection of the other two colors alternates every fourth row. Thus, for example, in the example shown, in two of each four consecutive rows, the color red 308 may be selected, while in the remaining two rows, blue 310 and green 312 may alternate every fourth row. Thus, if the array of pixels in the imager includes 256 rows and 256 columns, the device may transmit only 64 pixels, or every fourth pixel, for each row.

Figure 4:
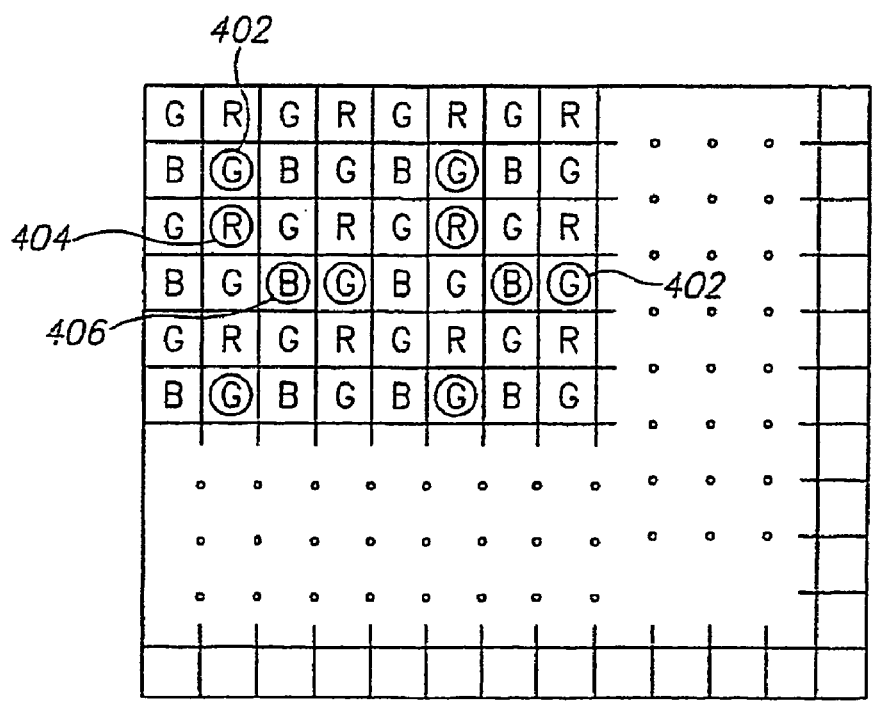
FIG. 4 depicts a schematic diagram of a second exemplary dilution pattern for selecting pixels according to an embodiment of the present invention.

FIG. 4 depicts another exemplary dilution pattern that may be used in accordance with embodiments of the invention. In this second exemplary dilution pattern, a pattern may be repeated every four rows, in which no pixels may be transmitted from a first row, every fourth pixel may be transmitted from each of the next two rows, and every second pixel may be transmitted from the fourth row. In this embodiment, it will be recognized that twice as many green pixels 402 may be transmitted than red pixels 404 or blue pixels 406.

According to some embodiments of the present invention, the device may transmit for some or all pixels the difference between the actual value and a predicted value based on the already determined values of other pixels, for example, neighboring pixels. The receiver may determine the predicted value based on the values of the other pixels, and modify the predicted value by the difference transmitted, thereby reconstructing the original actual value for the pixel. It will be recognized that this embodiment of the invention may be implemented as lossless or lossy. For example, in one embodiment, for each pixel there may be transmitted either a value or an exact difference based on a predicted value for the pixel. In such an embodiment, no image quality in the reconstructed image will be lost. In another example, there may be set a threshold, wherein a difference between the predicted value and the actual value that may be less than the threshold may not be transmitted. In this latter example, some image quality in the reconstructed image may be compromised.

It will be recognized by those of skill in the art that while only several dilution patterns have been discussed at length, any suitable dilution pattern that selects some pixels or areas for transmission while omitting others may be used in accordance with embodiments of this invention. In one embodiment of the invention, producing selected data includes for example modifying at least one input datum by reference to at least one other input datum to produce selected data.

Optionally, devices in accordance with embodiments of the invention may operate in a "simple" fast mode, an "averaging" fast mode or other suitable mode corresponding to any suitable dilution pattern, including, for example, the modes discussed herein. In "averaging" mode, the value transmitted for a selected pixel of a certain color may be summed or averaged or otherwise affected by the value of a nearby pixel, typically a pixel of the same color. For example, in FIG. 3, a pixel 308 selected by the particular dilution pattern for transmission may be averaged by the imager with a neighboring pixel of the same color 302 prior to transmission. Averaging may be performed by the compression module, for example, the imager, or by another component. This "averaging mode" may be activated or deactivated, for example, by a control bit intrinsic or extrinsic to the compression module, for example, the imager. It will be appreciated by those of skill in the art that any modification of an input pixel by reference to one or more neighboring pixels, for example a weighted average, may be used in accordance with the present invention.

Also optionally, in an embodiment of the present invention, there may be provided an error correction mechanism for detecting and correcting errors. In some embodiments, control or "overhead" information may be transmitted in addition to the pixels of each image, for example, information contained in a prefix header and/or suffix word. This control information may or may not be compressed. Various techniques of error correction are known, any of which may be used in connection with any embodiment of the present invention. In some embodiments of the invention, the imager may perform error correction encoding.

At the receiver end, various methods may be used in accordance with embodiments of the present invention to reconstruct an image from the diluted data transmitted. The method of reconstruction may vary, for example, depending on the dilution pattern chosen.

Figure 5:
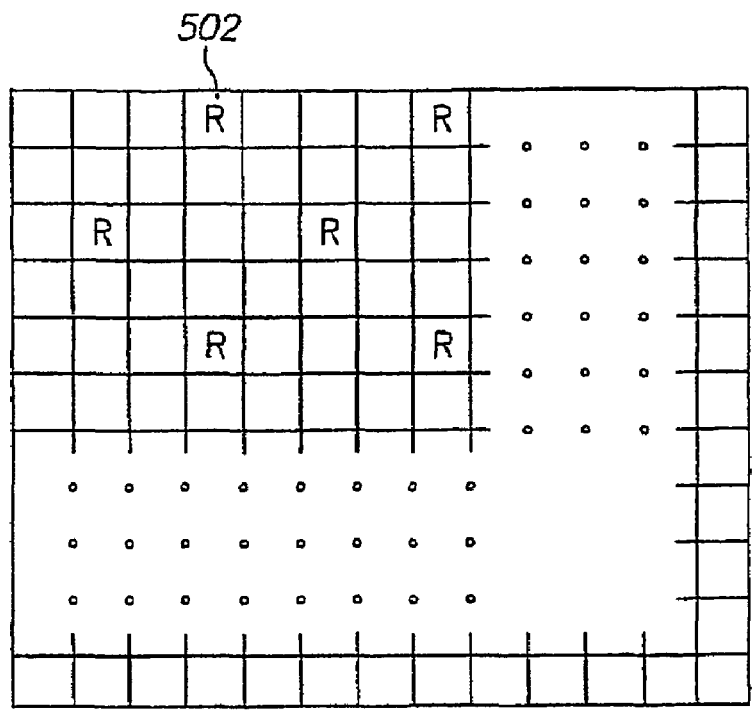
FIG. 5 depicts a schematic diagram of pixels of one color selected according to an exemplary dilution pattern in accordance with the present invention.

In an embodiment of the invention employing the first exemplary dilution pattern, a full matrix of color values for each pixel may be reconstructed from the selected pixels using various methods. In some embodiments of the invention, interpolation or weighted interpolation between selected data may be used for reconstructing the diluted image. Other suitable methods for reconstructing the data may be used in addition to interpolation or instead of interpolation. In one embodiment of the invention, edge detection may be used to determine weights for weighted interpolation when reconstructing an image from a diluted image. For example, as shown in FIG. 5, the sampled red pixels 502 in the first dilution pattern may be in a rhomboid pattern. In one embodiment of the present invention, some or all of the values of four pixels 602 forming a rhomboid may be used to calculate a value for the pixel at the center of the rhomboid, as depicted by the pixels 604 in FIG. 6. While in one embodiment of the present invention, the four values surrounding a rhomboid center may be averaged, other embodiments are of course possible. For example, edge detection or other suitable methods may be used to locate pixels that may be on the edge of an object. For pixels that may be determined to be on the edge, the center value may be determined by for example a weighted average of, for example, the four surrounding pixels. Whether the pixel may be on an edge may, for example, be determined based on the gradient at that pixel. Alternately or additionally, the center value may be determined by a weighted average of a subset of the surrounding pixels. In one embodiment, the center value may be determined based on the median of some or all of the surrounding pixels. In one embodiment, the interpolation may be on a grid not necessarily in the shape of a square. For example, the orthogonal values between the pixels may be obtained by interpolation of the four surrounding pixels. Any suitable method may be used for this interpolation, for example, linear, quadratic, bicubic, polynomial, weighted average, or other interpolation. The remaining pixels, which may be located on diagonals between originally selected pixels, may be interpolated using known methods. Interpolating typically helps to produces additional image data, eventually resulting in a reconstructed image.

Figure 6:
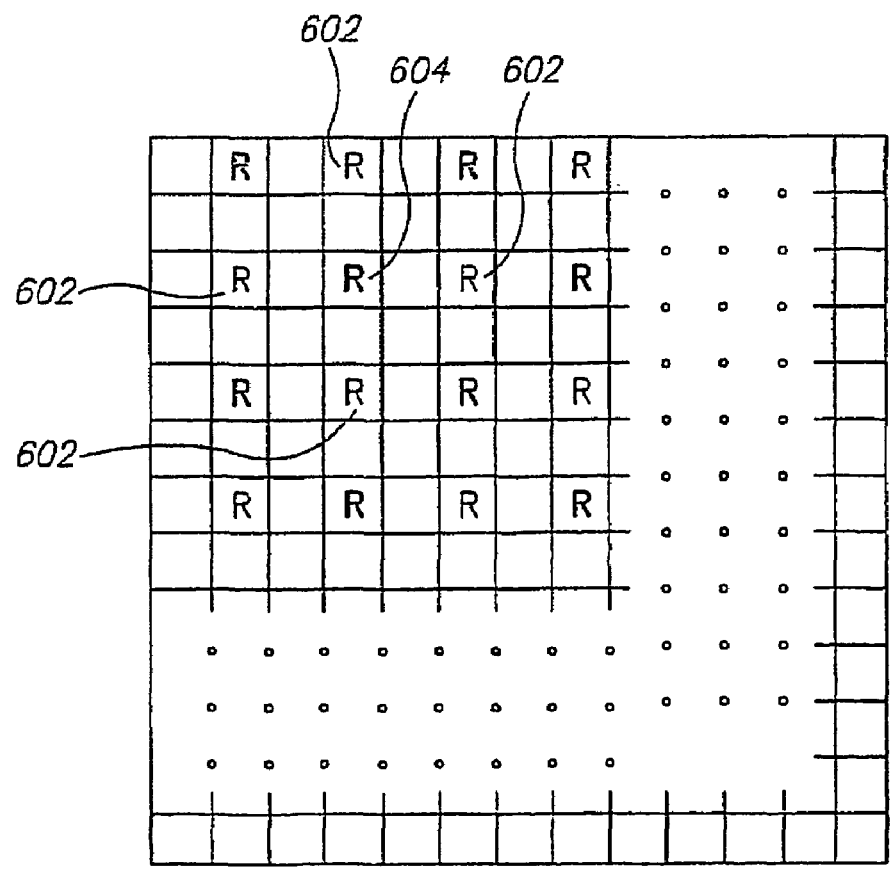
FIG. 6 depicts a schematic diagram of partial reconstruction of an image based on pixels selected according to an exemplary dilution pattern in accordance with the present invention.

With respect to the remaining two colors in the first dilution pattern, the missing pixels may be interpolated from the square pattern shown in FIG. 6 by any suitable method of interpolation, for example, linear, quadratic, bicubic, polynomial or other interpolation. The remaining pixels, which may be located on diagonals between originally selected pixels, may be for example, interpolated using known methods. While only some methods of interpolation of missing pixels have been enumerated, it will be understood by those of skill in the art that any suitable method of interpolation may be used consistent with any embodiment of the present invention.

With respect to reconstructing image data in accordance with the second exemplary dilution pattern, a similar reconstruction process may be used as the one described. Thus, for example, the rhomboid pattern created by the sampled green pixels may be similar to the rhomboid pattern of the red pixels in the first exemplary dilution pattern, and the pixels of the remaining two colors are in a square pattern. It will be understood by those of skill in the art that the present invention is not limited in the respect of the exemplary dilution patterns (and reconstruction schemes) described above, and that many others may be used in accordance with the present invention.

In some embodiments of the present invention, there may be further enhancement or refinement of the reconstructed image. In some embodiments of the present invention, the resulting image may be smoothed by modifying the color values of the originally selected pixels, for example, by replacing the original value by a weighted average of the original value taken together with some or all values of the surrounding selected pixels, for example, a median value of the surrounding pixels.

The various compression and/or dilution methods discussed herein need not be used with a device having more than one mode, or a "fast mode", but may be utilized for various other purposes. Further, compression and dilution of pixels need not be used together.

Typically, a compression and/or dilution process is carried out by control circuitry in the device 40, such as transmitter 41. Similarly, reconstruction and/or decompression may be carried out by for example, data processor 14, decompression module 610, processor 13, etc., or by structures in the receiver 12. Of course, in other embodiments, such processes may be earned out by other components, and of course the methods discussed herein may be earned out in devices having structures other than that of devices 40, receiver 12, and data processor 14. For example, control processes such as producing the selection of input data may be carried out by an imaging component, or another component. For example, a portion of a controller may be considered to be within the imaging unit.

Furthermore, in some embodiments of the present invention, enhancement may be made by for example modifying the intensity values of the image to restore them to near the original values. For example, the intensity of a reconstructed pixel may be calculated using only or predominantly the values of nearby originally selected pixels. In another embodiment, intensity for each pixel may be obtained by using the values of pixels of only one color, for example, green. It will be recognized that other methods of obtaining intensity values for reconstructed pixels may be used consistent with embodiments of this invention.

In some embodiments of the present invention, there may be lessening of color artifacts due to the process of dilution and reconstruction of the image, for example, by suppressing colors of pixels located on edges found in the image. In some embodiments of the invention, color suppression may also be used to correct color-saturated pixels during, for example, reconstruction.

In some embodiments of the present invention, a pre-processing block may be added for the original samples. For example, in one embodiment, a gradient evaluation for enhancing edges may be added. Additionally, in one embodiment of the invention, a post-processing block may be added for enhancing reconstruction, for example, for correcting interpolation artifacts, for example, periodic artifacts. In one embodiment, these artifacts may be corrected in the frequency domain by convolution or median filter.

Figure 7:
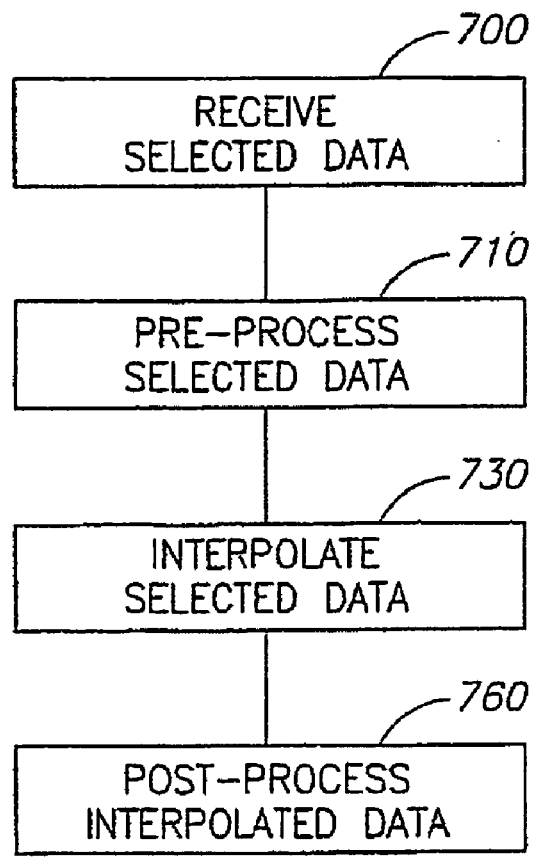
FIG. 7 depicts a series of steps of a method for reconstructing a diluted image according to an embodiment of the present invention.

FIG. 7 depicts a series of steps of a method for reconstructing a diluted image or other suitable data according to an embodiment of the present invention. Referring to FIG. 7, in block 700, selected data, for example a diluted image data, may be received. For example, the data may be received at a receiver 12, a data processor 14, or other suitable structure. In block 710 pre-processing may be preformed on data or selected data. Pre-processing may include for example, clearing errors with error correction code, reducing noise, performing a gradient evaluation for detecting and enhancing edges, calculating intensity, etc. Other suitable pre-processing may be used. In step 730, interpolation may be performed to, for example, fill in gaps between data. Interpolation may include, for example, linear, quadratic, bicubic, polynomial, weighted average, or other suitable interpolation. Edge information may be used to weight differently each of the samples. For example, pixels along directions with high gradient (possibly close to an edge) may, for example, not be included in interpolation. Other suitable weighting factors may be included. In one embodiment of the invention, intensity may be calculated and used during interpolation for maintaining the ratio between color and intensity during interpolation. Other suitable interpolation methods may be implemented. After interpolation, post-processing may be performed on interpolated data in block 760 to, for example enhance reconstructed image. Post-processing for enhancing a reconstructed image may include, for example image sharpening, color suppression, intensity adjustment, convolution or a median filter. Other suitable post-processing techniques may be implemented.

Embodiments of the present invention may include apparatuses for performing the operations herein. Such apparatuses may be specially constructed for the desired purposes (e.g., a "computer on a chip" or an ASIC), or may include general purpose computers selectively activated or reconfigured by a computer program stored in the computers. Such computer programs may be stored in a computer readable storage medium, such as, but is not limited to, any type of disk including floppy discs, optical disks, CD-ROMs, magnetic-optical discs, read-only memories (ROMs), random access memories (RAMs), electrically programmable read-only memories (EPROMs), electrically erasable and programmable read only memories (EEPROMs), magnetic or optical cards, or any other type of media suitable for storing electronic instructions.

The processes presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems appears from the description herein. In addition, embodiments of the present invention are not described with reference to any particular programming language. It will be appreciated that a variety of programming languages may be used to implement the teachings of the invention as described herein.

Unless specifically stated otherwise, as apparent from the discussions herein, it is appreciated that throughout the specification discussions utilizing terms such as "processing", "computing", "calculating", "determining", or the like, typically refer to the action and/or processes of a computer or computing system, or similar electronic computing device (e.g., a "computer on a chip" or ASIC), that manipulate and/or transform data represented as physical, such as electronic, quantities within the computing system's registers and/or memories into other data similarly represented as physical quantities within the computing system's memories, registers or other such information storage, transmission or display devices.

While the invention has been described with respect to a limited number of embodiments, it will be appreciated that many variations, modifications and other applications of the invention may be made. Embodiments of the present invention may include other apparatuses for performing the operations herein. Such apparatuses may integrate the elements discussed, or may comprise alternative components to carry out the same purpose. It will be appreciated by persons skilled in the art that the appended claims are intended to cover all such modifications and changes as fall within the true spirit of the invention.

The invention claimed is:

1. A system for reconstructing an image, the system comprising: a controller to:

receive selected image data from an in-vivo device, wherein said selected image data has been selected using a dilution pattern, wherein said dilution pattern is repeated in every four rows of the image, such that every second green pixel is selected from a first row, every second blue pixel is selected from a second row, and every second red pixel is selected from a third row, and wherein said dilution pattern further includes averaging a selected pixel with a neighboring pixel of the same color;

pre-process the selected image data by applying error correction code, gradient evaluation, or detecting edges;

interpolate the selected image data to produce reconstructed image data, so that the reconstructed image data includes more data than the selected image data; and post-process the reconstructed image data by applying a median filter.

2. The system of claim 1, wherein the controller interpolates by linear interpolation, quadratic interpolation, bicubic interpolation, polynomial interpolation, or weighted average interpolation.

3. The system of claim 1, wherein the controller is to produce additional image data resulting in reconstructed image data.

4. The system of claim 1, wherein the controller is further to post-process the reconstructed image data by color suppression.

5. The system of claim 1, wherein the controller is to generate reconstructed image data based on said selected image data.

6. The system of claim 1 wherein the controller is to receive the selected image data from a swallowable capsule.

7. The system of claim 1 wherein said selected image data is produced by an in vivo imager which captures a plurality of input data corresponding to an image.

8. The system of claim 7 wherein said selected image data is transmitted from an in vivo device via a transmitter.

9. The system of claim 1 wherein the dilution pattern used to select the selected image data is modified based on operating conditions of the in vivo device.

10. The system of claim 9 wherein the operating conditions are selected from a group consisting of: position of the in vivo device, pH, temperature, ambient lighting or color conditions.

11. The system of claim 1 wherein said dilution pattern further comprises selecting a same amount of red pixels and blue pixels and twice that amount of green pixels.

12. The system of claim 1 wherein said dilution pattern further comprises selecting every second green pixel from said second row, and selecting no pixels from a fourth row.

13. The system of claim 1 wherein said dilution pattern further comprises selecting every second red pixel from a fourth row, such that a same amount of green pixels and blue pixels are selected and twice that amount of red pixels are selected.

14. The system of claim 1 wherein said in-vivo device comprises an imager, and said averaging is performed by said imager.

15. The system of claim 1 wherein said in-vivo device comprises a control bit, and said averaging is activated or deactivated by said control bit.

* * * * *